US012722014B2

(12) United States Patent
Burnam

(10) Patent No.: US 12,722,014 B2
(45) Date of Patent: Sep. 1, 2026

(54) METHOD OF TREATING DRUG RESISTANT HYPERTENSION AND HEART FAILURE WITH PRESERVED EJECTION FRACTION BY COMBINED DRUG TREATMENT WITH BAROPACING AND BETA BLOCKERS

(71) Applicant: BaroPace, Inc., Ashland, OR (US)

(72) Inventor: Michael Burnam, Ashland, OR (US)

(73) Assignee: BaroPace, Inc., Ashland, OR (US)

( * ) Notice: Subject to any disclaimer, the term of this patent is extended or adjusted under 35 U.S.C. 154(b) by 299 days.

(21) Appl. No.: 18/256,841

(22) PCT Filed: Nov. 16, 2021

(86) PCT No.: PCT/US2021/059557
§ 371 (c)(1),
(2) Date: Jun. 9, 2023

(87) PCT Pub. No.: WO2022/125275
PCT Pub. Date: Jun. 16, 2022

(65) Prior Publication Data

US 2024/0017077 A1 Jan. 18, 2024

Related U.S. Application Data

(60) Provisional application No. 63/237,029, filed on Aug. 25, 2021, provisional application No. 63/123,951, filed on Dec. 10, 2020.

(51) Int. Cl.
*A61N 1/365* (2006.01)
*A61K 38/55* (2006.01)

(52) U.S. Cl.
CPC ........ *A61N 1/36564* (2013.01); *A61K 38/556* (2013.01)

(58) Field of Classification Search
CPC ........... A61N 1/36564; A61N 1/36542; A61N 1/39622; A61N 1/36535; A61N 1/3702; A61N 1/36585; A61N 1/395; A61N 1/3622; A61N 1/3627; A61N 1/3682; A61N 1/3684; A61N 1/36842; A61N 1/36843; A61N 1/3937; A61N 1/3987; A61N 1/057; A61N 1/36592; A61N 1/371; A61N 1/3712; A61N 1/37205; A61N 1/37518; A61N 1/3756; A61N 1/378; A61N 1/3925; A61K 38/556; A61K 45/06; A61P 9/00; A61P 9/12
See application file for complete search history.

(56) References Cited

U.S. PATENT DOCUMENTS

| | | | | |
|---|---|---|---|---|
| 5,225,401 | A | 7/1993 | Seymour | |
| 6,487,450 | B1 | 11/2002 | Chen | |
| 7,142,911 | B2 | 11/2006 | Boileau et al. | |
| 8,043,215 | B2 | 10/2011 | Zhang et al. | |
| 11,612,352 | B1 | 3/2023 | Kohli et al. | |
| 2003/0045910 | A1* | 3/2003 | Sorensen | A61N 1/36585 607/23 |
| 2004/0106953 | A1* | 6/2004 | Yomtov | A61M 5/14276 607/3 |
| 2004/0106954 | A1* | 6/2004 | Whitehurst | A61N 1/3627 607/3 |
| 2005/0137626 | A1 | 6/2005 | Pastore et al. | |
| 2009/0092964 | A1 | 4/2009 | Liggett | |
| 2011/0213435 | A1 | 9/2011 | Rom | |
| 2012/0035486 | A1 | 2/2012 | Zhang et al. | |
| 2019/0111014 | A1 | 4/2019 | Sturrock et al. | |
| 2019/0232065 | A1* | 8/2019 | Perschbacher | A61B 5/021 |
| 2019/0299004 | A1* | 10/2019 | Hahn | A61N 1/36585 |
| 2020/0305713 | A1 | 10/2020 | Sipe et al. | |
| 2022/0040487 | A1* | 2/2022 | Burnam | G16H 10/60 |
| 2026/0000900 | A1 | 1/2026 | Burnam et al. | |

FOREIGN PATENT DOCUMENTS

| | | | | |
|---|---|---|---|---|
| WO | 2004033036 | | 4/2004 | |
| WO | 2020096982 | A1 | 5/2020 | |
| WO | 2020210060 | A1 | 10/2020 | |
| WO | WO-2021194543 | A1 * | 9/2021 | A61N 1/3628 |

(Continued)

OTHER PUBLICATIONS

Stéphane Laurent, Antihypertensive drugs, Pharmacological Research, vol. 124, 2017, pp. 116-125, ISSN 1043-6618, https://doi.org/10.1016/j.phrs.2017.07.026. (https://www.sciencedirect.com/science/article/pii/S1043661817308460).

International Search Report and Written Opinion Issued in International Application No. PCT/US2021/059557, mailed on Mar. 17, 2022.

Office Action of IL Application No. 303494, dated Nov. 23, 2025, 5 pages.

Examination Report for Indian Patent Application No. 202447019877, dated Feb. 4, 2026, 9 pages.

Office Action for Canadian Patent Application No. 3204319, mailed Jan. 6, 2026, 5 pages.

Extended European Search Report and Written Opinion for Application No. 25201005.3 dated Feb. 20, 2026.

(Continued)

*Primary Examiner* — Carl H Layno
*Assistant Examiner* — Anh-Khoa N Dinh
(74) *Attorney, Agent, or Firm* — DLA Piper LLP (US)

(57) ABSTRACT

A method of treating a patient with drug resistant hypertension ("DRH") and/or heart failure with preserved ejection fraction ("HFpEF ") including the steps of: treating the patient with angiotensin converting enzyme inhibitor ("ACEI") and/or an angiotensin receptor blocking [ARB] drug and cardiac pacing the patient as controlled by an algorithm. Performance may be improved by simultaneously withholding administration of any beta-1 selective beta adrenergic blockers. The method may also include the steps of administering to a patient a therapeutic amount of a beta blocker having intrinsic sympathomimetic activity ("ISA") and pacing the heart of a patient using the algorithm.

20 Claims, No Drawings

(56) References Cited

FOREIGN PATENT DOCUMENTS

WO 2022046326 3/2022

OTHER PUBLICATIONS

Extended European Search Report for European Application No. 21904096.1, dated Jan. 26, 2024, 06 Pages.
International Preliminary Report on Patentability for International Application No. PCT/US2022/041289, dated Mar. 7, 2024, 10 Pages.
International Preliminary Report on Patentability for International Application No. PCT/US2021/059557, dated on Jun. 22, 2023, 11 Pages.
International Search Report and Written Opinion for International Application No. PCT/US2022/041289, dated Nov. 29, 2022, 13 Pages.
Examination Report for Indian Patent Application No. 202347044987, dated Jul. 17, 2026, 9 Pages.

* cited by examiner

METHOD OF TREATING DRUG RESISTANT HYPERTENSION AND HEART FAILURE WITH PRESERVED EJECTION FRACTION BY COMBINED DRUG TREATMENT WITH BAROPACING AND BETA BLOCKERS

CROSS-REFERENCE TO RELATED APPLICATIONS

This application is a National Stage Application under 35 U.S.C. § 371 of International Application No. PCT/US2021/059557, filed Nov. 16, 2021, published as WO 2022/125275 A1, which claims priority to U.S. Provisional Application No. 63/237,029, filed on Aug. 25, 2021, and U.S. Provisional Application No. 63/123,951, filed on Dec. 10, 2020, the entireties of each of which are incorporated herein by reference.

This application claims priority to, and the benefit of the earlier filing date of: US provisional patent application entitled, A METHOD OF TREATING DRUG RESISTANT HYPERTENSION AND HEART FAILURE WITH PRESERVED EJECTION FRACTION BY COMBINED DRUG TREATMENT WITH BAROPACING, filed on Dec. 10, 2020, Ser. No. 63/123,951, and entitled, BETA BLOCKERS AND BAROPACING, filed on Aug. 21, 2021, Ser. No. 63/237,029 pursuant to 35 USC 119, the contents of all of which are incorporated herein by reference.

FIELD OF THE TECHNOLOGY

The invention relates to the field of cardiac pacing and drug administration in combination and to methods and apparatus for pacing a heart to treat drug resistant hypertension and heart failure with preserved ejection fraction (HFpEF).

BACKGROUND

Beta-adrenergic blocking drugs (beta blockers) are an important element of the standard treatment guidelines for multiple cardiovascular conditions, including ischemic heart disease, heart failure, cardiac rhythm disturbances, stroke, and hypertension. Three pharmacologic subtypes of beta blockers are relevant, including: non-selective e.g. Propranolol); beta-1 selective (beta 1>beta 2, e.g. Metoprolol, Carvedilol; and beta blockers with intrinsic sympathomimetic activity (ISA) e.g. Pindolol and Acebutolol. Beta blockers with ISA do not lower heart rate to the same extent as beta-1 selective agents. The U.S. beta blocker market is dominated by Metoprolol and Carvedilol.

Beta blockers, also known as beta-adrenergic blocking agents, are medications that multiple clinical uses, including reducing blood pressure, reducing the incidence of some cardiac arrhythmias, treating migraine headaches, and anxiety. Beta blockers work by competitively blocking the effects of the hormone epinephrine, also known as adrenaline. Beta blockers cause the heart to beat more slowly and with less force, which lowers blood pressure.

Some Beta blockers have also been shown to reduce mortality after heart attacks. Beta blockers are a class of drugs that works by competitively (reversibly) blocking the neurotransmitters norepinephrine and epinephrine from binding to receptors. There are three known types of beta receptors, known as beta1 (β1), beta2 (β2) and beta3 (β3).

β1-adrenergic receptors are located commonly in the heart and kidneys. β2-adrenergic receptors are located mainly in the lungs, gastrointestinal tract, liver, uterus, vascular smooth muscle, and skeletal muscle. β3-adrenergic receptors are located in fat cells.

When the neurotransmitters are prevented from binding to the receptors, it in turn causes the effects of adrenaline (epinephrine) to be blocked. This action allows the heart to relax and beat more slowly (reduces cardiac work) thereby reducing heart muscle oxygen consumption.

Individual compounds within the class of Beta blockers differ by which receptors are blocked. First generation beta blockers such as propranolol (Inderal, InnoPran), nadolol (Corgard), timolol maleate (Blocadren), penbutolol sulfate (Levatol), sotalol hydrochloride (Betapace), and pindolol (Visken) are non-selective, meaning that they block both beta1 (β1) and beta2 (β2) receptors and will subsequently affect the heart, kidneys, lungs, gastrointestinal tract, liver, uterus, vascular smooth muscle, and skeletal muscle and as an effect, and could cause reduced cardiac output, reduced renal output amongst other actions. Second generation beta blockers such as metoprolol (Lopressor, Toprol XL), acebutolol hydrochloride (Sectral), bisoprolol fumarate (Zebeta), esmolol hydrochloride (Brevibloc), betaxolol hydrochloride (Kerlone), and acebutolol hydrochloride (Sectral) are selective, as they block only β1 receptors and as such will affect mostly the heart and cause reduced heart rate, cardiac contractility, and cardiac output.

Beta blockers such as pindolol (Visken), penbutolol sulfate (Levatol), and acebutolol hydrochloride (Sectral) differ from other beta blockers as they possess intrinsic sympathomimetic activity (ISA), which means they to some degree mimic the effects of epinephrine and norepinephrine and can cause an increase in heart rate and less of a blood pressure lower effect. ISA's have smaller effects in reducing resting cardiac output and resting heart rate, in comparison to drugs that do not possess ISA.

Beta-1 selective beta blockers are commonly used in patients with angina pectoris, chest pain due to blocked or narrowed coronary arteries to reduce the frequency and severity of chest pain and prevent progression to acute myocardial infarction. Beta blockers with ISA lack this effect and may in fact increase the frequency and severity of angina pectoris in patients with atherosclerotic coronary artery disease, largely for this reason, beta blockers with ISA are no longer used to treat hypertension in favor of beta-1 selective agents. The problem is that the two most commonly prescribed beta blocking drugs, the beta-1 selective agents Metoprolol and Carvedilol block the beneficial effects of BaroPacing in hypertension and HFpEF associated with hypertension, the most common cause of HFpEF.

BRIEF SUMMARY

Based on the observation that pacemaker implant in patients with drug resistant hypertension (DRH) and heart failure with preserved ejection fraction (HFpEF) lowers blood pressure and improves clinical outcomes, BaroPace, Inc. is developing technology to treat drug resistant hypertension and (HFpEF) by regulating cardiac pacemakers in real time in response to blood pressure (BaroPacing™). Published retrospective and a prospective study of BaroPacing (see abstract submitted to the American College of Cardiology, Control/Tracking Number: 22-A-13540-ACC, Activity: ACC Abstract) by BaroPace's clinical research team show that current treatment with both Metoprolol and Carvedilol substantially blunts the beneficial blood pressure lowering effects of BaroPacing, as well as the improvement in New York Heart Association Class seen in HFpEF. If a slow heart rate (bradycardia) is the missing link in the development of hypertension and later HFpEF as BaroPace believes, a beta blocker with ISA may be clinically superior to the market leading drugs that cause greater bradycardia. The BaroPacing research model offers a now-proven cost efficient means of screening ISA drugs such as pindolol and acebutolol to test this hypothesis. If proven true, besides a new patentable indication, such results could lead to a treatment paradigm shift and clinical revitalization of ISA beta blockers.

The illustrated embodiments of the invention are directed to a method of treating a patient with DRH and/or HFpEf including the steps of: treating the patient with angiotensin converting enzyme inhibitor (ACEI) and/or an angiotensin receptor blocking [ARB] drug without or with other accepted treatment modalities (hereinafter defined as "conventional treatment modalities") alone or in combination, including but not limited to diuretics, calcium channel blocking agents, alpha adrenergic blocking agents, aldosterone blocking or inhibiting drugs, and an angiotensin receptor neprilysin inhibitor (ARNI) alone or in combination with an ARB or ACEI and cardiac pacing the patient as controlled by a BaroPace algorithm.

The method further includes the step of withholding treatment of the patient with a beta-1 selective beta adrenergic blocking drug.

The method further includes the step of including a beta adrenergic blocking drug with ISA.

The step of cardiac pacing the patient as controlled by a BaroPace algorithm comprises monitoring the patient in combination with BaroPacing or PressurePace AI using trend analysis, or Stimulus Architecture Algorithm (SAA), as defined and disclosed in "An Intelligently, Continuously And Physiologically Controlled Pacemaker And Method Of Operation Of The Same", International Pat. App. PCT/US20/25447; and "Method of Treatment of Drug Resistant Hypertension by Electrically Stimulating the Right Atrium to Create Inhibition of the Autonomic Nervous System," International Pat. Appl., PCT/US20/44784, both incorporated herein by reference.

The method further includes using the method to treat cardiac arrhythmias and reduce or prevent sudden cardiac death.

The method further includes using the method to prevent hypertensive stroke, intracranial bleeding due to hypertension, arterial aneurysm formation due to hypertension, and hypertensive renal dysfunction.

Another characterization of the illustrated embodiments include a method of providing a cardiac treatment for a patient including the steps of: sensing the cardiac activity of the patient; processing the sensed cardiac activity using trend analysis or Stimulus Architecture Algorithm (SAA) as controlled by artificial intelligence; pacing the patient using BaroPacing; simultaneously treating the patient with a class of drugs, that without BaroPacing does not produce a therapeutic response; and at the same time eliminating one or more other selected drug classes to further improve treatment benefits.

The step of treating the patient using a class of drugs includes the step of treating a patient with ACEI/ARB provides a therapeutic drug effect not present without BaroPacing, and removing the adverse effects on heart rate modulation experienced with beta-1 selective beta blockers, which are eliminated from the treatment protocol.

The illustrated embodiment are also characterized as a method of treating a patient with DRH and/or HFpEf including the steps of: BaroPacing the patient; and administering to the patient a therapeutically effective amount of angiotensin converting enzyme inhibitor (ACEI) and/or an angiotensin receptor blocking [ARB] drug while BaroPacing, including but limited to the pharmacologic conventional treatment modalities listed above.

The method further includes withholding administration of any beta blocker to the patient during BaroPacing.

The method further includes administering a beta-adrenergic blocking drug with ISA without or with the conventional treatment modalities listed above.

Based upon his observations of patients with Drug Resistant Hypertension and pacemakers, modeling human physiology using "Ohm's Law" a missing link in the treatment of drug resistant hypertension is revealed as being the critical importance of heart rate. Ohm's Law applied to fluid flow in the heart gives the relationships:

$$V=IR;$$

Blood Pressure=(Cardiac Output)×(the Resistance to blood flow); and

Cardiac Output=(Heart Rate)×(Stroke Volume, which is the amount of blood pumped with each heart beat).

Heart Rate (HR) falls with aging due to deterioration of the heart's natural pacemaker. Blood Pressure (BP) is initially maintained by increasing Stroke Volume (SV). But if SV can't increase to compensate, BP is dependent on increasing Resistance (R), also known as peripheral resistance, the pathophysiologic hallmark of hypertensive disease.

The aging heart loses the ability to increase SV. Couple this with a falling HR, and peripheral resistance (R) must increase. Increasing R creates a viscous cycle. The higher the R, the harder the heart must work to push blood against it. This leads to more thickening and stiffening of the heart muscle that eventually reduces SV further, and the heart fails. Based upon the theory proposed in the illustrated embodiments of the invention here and clinical data from more than two hundred patients, I believe that a falling HR is the missing link in the treatment of both drug resistant hypertension and the commonest form of heart failure.

I have prospectively studied 14 subjects with hypertension and dual chamber pacemakers, 6 not taking any beta blockers, and 8 taking either metoprolol or carvedilol. BaroPacing, increasing the right atrial pacing rate according to BaroPace Inc.'s patent-pending algorithm, aka PressurePace or PressurePacing™, significantly lowered systolic blood pressure (>10 mmHg) in the 6 subjects not taking Carvedilol or Metoprolol ($p<0.004$), This effect was lost in the 8 patients taking either Metoprolol or Carvedilol. PressurePacing or BaroPacing is defined to include the algorithmically controlled pacing methodologies and programmable pacemakers as disclosed in PCT/US19/59703; PCT/US20/025447; PCT/US21/42622; and US Provisional filing 63/123,951, each and all incorporated herein by reference.

Because BaroPacing as a treatment for hypertension and HFpEF depends upon the restoration of physiologic heart rate through cardiac pacing, and is prevented by beta-1 selective beta blockers that drop heart rate, contrary to the expectations and assumptions of the medical profession in regard to ISA beta blockers, it is reasonable to expect that beta blockers with ISA activity, currently thought by the medical profession to be essentially worthless in the marketplace, can be a useful adjunct with BaroPacing in the treatment of hypertension and HFpEF in patients without angina pectoris.

The scope of the illustrated embodiments also extends to a system for operating a therapeutic device using any one of the above methods.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The disclosure can be better visualized by turning now to the following drawings wherein like elements are referenced by like numerals.

DETAILED DESCRIPTION OF THE PREFERRED EMBODIMENTS

It has only recently been found that the concurrent use of a beta-1 selective adrenergic blocking drug in patients with drug resistant hypertension (DRH) and/or heart failure with preserved ejection fraction (HFpEf) negates the beneficial effect of conventional pacing therapies, as predicted by the "BaroPace Effect" that states that any maneuver or drug that lowers heart rate has an adverse effect, likely by increasing peripheral resistance. The negative effect of a beta-1 selective beta blocker on a conventionally paced patient is seen as: 1) a failure to lower blood pressure with pacing; 2) a failure to improve New York Heart Association Functional Classification or NYHA Class with pacing; and 3) an increase in hospitalizations for HFpEF, and 4) the continued need for maximal drug therapy. Because beta-1 selective beta adrenergic blocking drugs are a primary focus of all therapeutic guidelines for treatment of both DRH and HFpEF, this finding has profound implications.

The concurrent use of an angiotensin converting enzyme inhibitor (ACEI) and/or an angiotensin receptor blocking [ARB] drug in the same subsets of pacing patients significantly improves the same categories of outcomes when combined with "BaroPacing", which is defined herein as a pacing method using AI or using a pacing method without AI to identify a trend analysis using a stimulus architecture algorithm (SAA), as disclosed in "An Intelligently, Continuously And Physiologically Controlled Pacemaker And Method Of Operation Of The Same", International Pat. App. PCT/US20/25447; and/or "Method of Treatment of Drug Resistant Hypertension by Electrically Stimulating the Right Atrium to Create Inhibition of the Autonomic Nervous System," International Pat. Appl., PCT/US20/44784, both incorporated herein by reference, including in particular the drawings and related textual material therefrom which illustrate various ones of the claims below.

Therefore, the combination of a pacemaker regulated according to the BaroPace or PressurePace AI methods provides an improved method of treatment for DRH and HFpEF, and also likely improves exercise tolerance in both subsets of patients.

ACEIs and ARBs reduce blood pressure in normal patients by blocking the effect of the natural vasoconstrictive substance angiotensin. An ACEI blocks the conversion of the inactive form of angiotensin to its active form. An ARB blocks the receptor for angiotensin preventing it from producing an effect. Angiotensin has no effect on heart rate at useful dosages. However, ACEIs and ARBs alone have no beneficial effect in DRH and HFpEF patients. The combination of the ANI inhibitor sacubitril with the ARB valsartan was recently approved as an adjunct drug therapy for the treatment of HFpEF.

Beta blockers block the effect of the hormones epinephrine and norepinephrine by occupying their receptors. The effects "epi" and "norepi" are complex and include an increase in heart rate which is dose dependent, an increase in blood pressure by direct vasoconstriction different from angiotensin, an increase in cardiac contractility, vasoconstriction in the gut blood flow which "isn't needed" during fight or flight, and more. Beta-1 selective beta adrenergic blockers are "bad" for HFpEF and DRH patients because they lower heart rate. Beta adrenergic blocking drugs with ISA may be either less deleterious or beneficial because they do not lower heart rate to the same drug, or at all. ACEIs and ARBs are probably "good" because they reduce resistance without doing anything else, such as lowering heart rate.

More importantly, there is no direct evidence of any one or combination of ACEI/ARBs improve HFpEF, NYHA class or reduce hospitalizations. Surprisingly, it is only when you combine ACEI/ARBs with BaroPacing that you unlock the therapeutic potential of the drugs. This is further amplified when you withhold or remove the negative effect of beta-1 selective beta blockers.

ACEIs/ARBs have heretofore no documented beneficial effect in HFpEF or DRH patients, who were conventionally paced. This new effect with BaroPacing is seen objectively in our data. The effect is striking in the case of DRH patients. Drug resistant hypertension means by definition, that even in the presence of ACEI/ARBS, the hypertension is still resistant. By definition the drugs aren't working. Add BaroPacing and the drugs have the same beneficial effects as they do in other patients. The combination of BaroPacing plus ACEI/ARB treatment gives rise to a new method to treat DRH patients.

In the case of HFpEF, the most recent American College of Cardiology position statement on HFpEF begins by saying, in essence, that nothing is known to work, either in drugs or devices, to treat HFpEF, with the exception of sacubitril/valsartan. Add BaroPacing to one of the drug classes and subtract beta-1 selective beta blockers, and a clear beneficial effect of ACE/ARB's in HFpEF patients becomes demonstrable. No such relationship for ACE/ARB's without sacubitril is known to exist absent the BaroPacing. The combination of sacubitril with valsartan is known to be associated severe side effects, including hyperkalemia, hypotension, and increased serum creatinine. Other side effects include: acute kidney injury, and renal failure syndrome. Thus, while sacubitril/valsartan is approved for use in HFpEF, the combination of BaroPacing alone or with an ACEI or ARB alone or in combination with the conventional treatment modalities listed above offers much less risk of an adverse event.

Again the combination of BaroPacing and ACEI/ARBs and the absence of beta blockers forms a new method for the treatment of HFpEF patients that can't be demonstrated for the ACEI/ARB without BaroPacing.

We have previously published retrospective data in patients with permanent pacing and drug resistant hypertension (HTN), showing a significant decline in systolic BP (SBP) that was strongly correlated with atrial pacing. It has also been reported that cardiac pacing inhibits sympathetic autonomic nerve activity. In an office-based study, we tested the acute effects of increasing atrial pacing rate in patients with pre-existing HTN and permanent pacemakers.

A total of 12 patients with HTN and previously implanted pacemakers for routine clinical indications were included in this study. Patients with atrial fibrillation were excluded. After a one-hour rest period, atrial pacing was increased by 10% over baseline atrial pacing or sensing rate every 15 minutes. If the SBP did not decline by >10 mmHg, pacing rate was increased by additional 10% increments for a maximal total of four interventions/patient, when applicable. If SBP declined by >10 mmHg at any stage, no further pacing changes were made.

A total of 33 treatment events, i.e., changes in programmed atrial pacing rate, were performed in the 12 patients. Mean drop in SBP was 8.1±7.5 mmHg; diastolic BP (DBP) declined 6.1±3.6 mmHg ($p<0.01$). Patients taking beta-1 selective beta blockers (BIB) were significantly less likely to show this effect (63% interventions vs 14%, B1B vs no B1B, $p=0.01$). No patient on B1B therapy showed a SBP decline>10 mmHg vs 37% treatment events in patients not on BB ($p=0.013$).

In hypertensive patients, incremental atrial pacing results in significant acute drops in SBP and DBP. This effect is largely blocked by chronic beta-1 selective beta blocker therapy. The latter may be secondary to a pre-existing low sympathetic tone in patients treated with beta blockers. The results of this preliminary study suggest that further investigation of atrial pacing in patients with HTN is warranted. As well, the current paradigm of treating HTN with B1B may not apply to patients with permanent atrial pacing.

Many alterations and modifications may be made by those having ordinary skill in the art without departing from the spirit and scope of the embodiments. Therefore, it must be understood that the illustrated embodiment has been set forth only for the purposes of example and that it should not be taken as limiting the embodiments as defined by the following embodiments and its various embodiments.

Therefore, it must be understood that the illustrated embodiment has been set forth only for the purposes of example and that it should not be taken as limiting the embodiments as defined by the following claims. For example, notwithstanding the fact that the elements of a claim are set forth below in a certain combination, it must be expressly understood that the embodiments includes other combinations of fewer, more or different elements, which are disclosed in above even when not initially claimed in such combinations. A teaching that two elements are combined in a claimed combination is further to be understood as also allowing for a claimed combination in which the two elements are not combined with each other, but may be used alone or combined in other combinations. The excision of any disclosed element of the embodiments is explicitly contemplated as within the scope of the embodiments.

The words used in this specification to describe the various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the embodiments.

I claim:

1. A method of treatment, the method comprising:

administering one or more of an angiotensin converting enzyme inhibitor (ACEI) treatment and an angiotensin receptor blocking (ARB) treatment to a patient;

administering a beta blocker intrinsic sympathomimetic activity (ISA) treatment to the patient;

receiving a first blood pressure value at a first time subsequent to providing the at least one or more of the ACEI treatment and the ARB treatment and subsequent to providing the ISA treatment;

determining that the first blood pressure value deviates from a target blood pressure value by at least a threshold amount;

determining a first pacing rate of a pacing device based on the first blood pressure value and an artificial intelligence (AI) trend analysis;

outputting the first pacing rate to the pacing device; and administering, by the pacing device, a first pacing therapy to the patient based on the first pacing rate.

2. The method of claim 1, wherein determining the first pacing rate of the pacing device is performed in real-time upon receiving the first blood pressure value or determining that the first blood pressure deviates from the target blood pressure value by at least the threshold amount.

3. The method of claim 1, wherein the first pacing rate is approximately 10% greater than a baseline atrial pacing rate.

4. The method of claim 1, further comprising:

receiving a second blood pressure value at a second time subsequent to the first time;

determining that the second blood pressure value deviates from the target blood pressure value by at least the threshold amount;

determining a second pacing rate of the pacing device; and outputting the second pacing rate to the pacing device.

5. The method of claim 4, further comprising:

administering, by the pacing device, a second pacing therapy to the patient based on the second pacing rate.

6. The method of claim 1, wherein the first blood pressure value is a systolic blood pressure (SBP) value.

7. The method of claim 1, further comprising:

receiving a second blood pressure value at a second time subsequent to the first time;

determining that the second blood pressure value is one of: within the threshold amount of the target blood pressure value, lower than the first blood pressure value by a threshold pressure value; and maintaining the first pacing rate of the pacing device.

8. A system for providing treatment comprising:

a first module configured to administer one or more of an angiotensin converting enzyme inhibitor (ACEI) treatment and an angiotensin receptor blocking (ARB) treatment to a patient;

a second module configured to provide administer a beta blocker intrinsic sympathomimetic activity (ISA) treatment to the patient;

a pacing device configured to output electric pacing signals based on pacing rates; and at least one processor operatively coupled to a memory storing computer-readable instructions that, when executed by the at least one processor, cause the at least one processor to:

receive a first blood pressure value at a first time subsequent to providing the one or more of the ACEI treatment and the ARB treatment and subsequent to providing the ISA treatment;

determine that the first blood pressure value from a target blood pressure value by at least a threshold amount;

based on the first blood pressure value and an artificial intelligence (AI) trend analysis executed by an AI module, and output the first pacing rate to the pacing device; and the pacing device configured to administer a first pacing therapy to the patient based on the first pacing rate.

9. The system of claim 8, wherein the computer-readable instructions, when executed by the at least one processor, further cause the at least one processor to determine the first pacing rate of the pacing device in real-time upon receiving the first blood pressure value or determining that the first blood pressure value deviates from the target blood pressure value by at least the threshold amount.

10. The system of claim 8, wherein the first pacing rate is approximately 10% greater than a baseline atrial pacing rate.

11. The system of claim 8, wherein the computer-readable instructions, when executed by the processor, further cause the at least one processor to:

receive a second blood pressure value at a second time subsequent to the first time;

determine that the second blood pressure value deviates from the target blood pressure value by at least the threshold amount; and determine a second pacing rate of the pacing device; and output the second pacing rate to the pacing device.

12. The system of claim 11, wherein the computer-readable instructions, when executed by the processor, further cause the at least one processor to:

administer a second pacing therapy to the patient based on the second pacing rate.

13. The system of claim 8, wherein the first blood pressure value is a systolic blood pressure (SBP) value.

14. The system of claim 8, wherein the computer-readable instructions, when executed by the processor, further cause the at least one processor to:

receive a second blood pressure value at a second time subsequent to the first time;

determine that the second blood pressure value is one of:

within the threshold amount of the target blood pressure value and lower than the first blood pressure value by a threshold pressure value; and maintain the first pacing rate of the pacing device.

15. A system comprising:

a pacing device configured to output electric pacing signals based on pacing rates; and at least one processor operatively coupled to a memory storing computer-readable instructions that, when executed by the at least one processor, cause the at least one processor to:

receive a first blood pressure value from a patient at a first time subsequent to administration of one or more of an angiotensin converting enzyme inhibitor (ACEI) treatment and an angiotensin receptor blocking (ARB) treatment to the patient and subsequent to administration of a beta blocker intrinsic sympathomimetic activity (ISA) treatment to the patient;

determine that the first blood pressure value deviates from a target blood pressure value by at least a threshold amount;

determine a first pacing rate of a pacing device based on the first blood pressure value and an artificial intelligence (AI) trend analysis executed by an AI module, and output the first pacing rate to the pacing device; and the pacing device configured to administer a first pacing therapy to the patient based on the first pacing rate.

16. The system of claim 15, wherein the computer-readable instructions, when executed by the processor, further cause the at least one processor to:

receive a second blood pressure value at a second time subsequent to the first time;

determine that the second blood pressure value deviates from the target blood pressure value by at least the threshold amount;

determine a second pacing rate of the pacing device; and output the second pacing rate to the pacing device.

17. The system of claim 16, wherein the computer-readable instructions, when executed by the processor, further cause the at least one processor to:

administer a second pacing therapy to the patient based on the second pacing rate.

18. The system of claim 15, wherein the computer-readable instructions, when executed by the processor, further cause the at least one processor to:

receive a second blood pressure value at a second time subsequent to the first time;

determine that the second blood pressure value is one of:

within the threshold amount of the target blood pressure value and lower than the first blood pressure value by a threshold pressure value; and maintain the first pacing rate of the pacing device.

19. The system of claim 15, wherein the computer-readable instructions, when executed by the at least one processor, further cause the at least one processor to determine the first pacing rate of the pacing device in real-time upon receiving the first blood pressure value or determining that the first blood pressure value deviates from the target blood pressure value by at least the threshold amount.

20. The system of claim 15, wherein the first pacing rate is approximately 10% greater than a baseline atrial pacing rate.

* * * * *